(12) United States Patent
Harada et al.

(10) Patent No.: US 8,273,229 B2
(45) Date of Patent: Sep. 25, 2012

(54) HYDROGEN QUANTITY SENSOR AND HYDROGEN STORAGE DEVICE USING THE SAME

(75) Inventors: Shuuji Harada, Niigata (JP); Tsuyoshi Suda, Niigata (JP)

(73) Assignee: Niigata TLO Corporation, Niigata (JP)

( * ) Notice: Subject to any disclaimer, the term of this patent is extended or adjusted under 35 U.S.C. 154(b) by 684 days.

(21) Appl. No.: 11/990,277

(22) PCT Filed: Apr. 11, 2006

(86) PCT No.: PCT/JP2006/307593
§ 371 (c)(1),
(2), (4) Date: Jul. 7, 2009

(87) PCT Pub. No.: WO2007/020732
PCT Pub. Date: Feb. 22, 2007

(65) Prior Publication Data
US 2009/0309603 A1 Dec. 17, 2009

(30) Foreign Application Priority Data
Aug. 12, 2005 (JP) ................................. 2005-234523

(51) Int. Cl.
*G01N 27/26* (2006.01)
(52) U.S. Cl. ..................................................... 204/431
(58) Field of Classification Search .................. 204/431, 204/433, 421, 432; 324/438
See application file for complete search history.

(56) References Cited

U.S. PATENT DOCUMENTS

| 2004/0074144 A1* | 4/2004 | Isogai et al. .................... 48/174 |
| 2005/0016866 A1* | 1/2005 | Kramer et al. ................. 205/637 |

FOREIGN PATENT DOCUMENTS

| JP | 63-281041 | 11/1988 |
| JP | 64-31044 | 2/1989 |
| JP | 10-282047 | 10/1998 |

OTHER PUBLICATIONS

International Search Report issued Jun. 27, 2006 in the International (PCT) Application of which the present application is the U.S. National Stage.

* cited by examiner

*Primary Examiner* — Jeffrey T Barton
*Assistant Examiner* — Louis Rufo
(74) *Attorney, Agent, or Firm* — Wenderoth, Lind & Ponack, L.L.P.

(57) ABSTRACT

A hydrogen quantity sensor can directly measure hydrogen contained in a hydrogen storage device with simple and easy means. The hydrogen quantity sensor comprises a detecting electrode comprised of a hydrogen storage alloy disposed inside a hydrogen storage vessel, a standard electrode disposed to confront the detecting electrode; and an electrolyte member disposed between the detecting electrode and the standard electrode. The detecting electrode, the standard electrode and the electrolyte member constitute a sensor portion to measure hydrogen concentration within the hydrogen storage alloy as an electromotive force value.

6 Claims, 6 Drawing Sheets

HYDROGEN QUANTITY SENSOR AND HYDROGEN STORAGE DEVICE USING THE SAME

FIELD OF THE INVENTION

This invention relates to a hydrogen quantity sensor that is suitable for use in a hydrogen fuel gas container or the like, and a hydrogen storage device using such a sensor.

BACKGROUND OF THE ART

It is desired in a future hydrogen energy utilizing society to develop a convenient and safe hydrogen storage system using hydrogen storage alloys, from which the hazardous nature of hydrogen explosion is removed. The hydrogen storage alloys are promising for use as a hydrogen fuel container for fuel cell driven vehicles because the hydrogen storage alloy has a higher storing efficiency than the containers storing hydrogen in a gaseous state, and it can prevent accidents resulting from intensive hydrogen gas leakage. When the hydrogen storage alloy is used as a hydrogen fuel container, it is necessary to provide a measuring device detecting residual hydrogen content within the container. It is desirable that the sensor can quantitatively monitor the hydrogen content within the hydrogen storage alloy at a wide temperature range spanning from room temperature to a hydrogen delivery temperature of the hydrogen storage alloy.

One of the conventional methods for detecting hydrogen is to measure hydrogen gas pressure. However, since the hydrogen delivery rate is usually controlled by adjusting the temperature of the hydrogen storage alloy, the hydrogen gas pressure varies widely during operation depending on the temperature. Thus, it is difficult to precisely measure the amount of hydrogen remaining in the storage device by measuring the gas pressure.

Another method is to utilize a flow integrator, which sums up the total gas delivery amount, so that by extracting the total gas delivery amount from initial storage amount, the residual amount is defined. However, this process, seemingly effective, is an indirect process so that it is necessary to use it concomitantly with other direct measuring processes.

Other available techniques for directly measuring the hydrogen content in the hydrogen storage alloy includes a gravimetric technique (measuring total mass of the metal) or measuring the lattice expansion of the alloy metal accompanied by the hydrogenation process. However, since the hydrogen mass is one hundredth lighter than that of the metal, and the lattice expansion is small enough to vary within the elastic limit of the alloy, these methods are not sufficient for quantitative measurement. Other methods such as measuring electric resistance or thermal conductivity of the metal are thinkable, however, these methods are not deemed reliable because they still leave unsolved problems such as fracturing of the alloy due to hydrogenation.

In addition, it is anticipated that the hydrogen fuel container utilizing the hydrogen storage alloy will be, in the future, commercialized as a cassette-type container because of its handling convenience. Therefore, the hydrogen quantity sensor is preferably assembled in the cassette-type container as a fuel hydrogen indicator for indicating hydrogen content within the hydrogen container.

DISCLOSURE OF THE INVENTION

Problem to be Solved by the Invention

The present invention has been achieved under the above-mentioned circumstances. It is an object of the present invention to provide a hydrogen quantity sensor that can directly measure the content of hydrogen remaining within the hydrogen storage device with simple and easy means. It is another object of the invention to provide a hydrogen quantity sensor that can quantitatively monitor the hydrogen content within the hydrogen storage alloy at a wide temperature range spanning from a room temperature to a hydrogen delivery temperature.

Means to Solve the Problem

In order to solve the problems described above, the hydrogen quantity sensor defined in a first aspect of the invention comprises: a detecting electrode comprised of a hydrogen storage alloy disposed inside a hydrogen storage vessel; a standard electrode disposed to confront the detecting electrode; and an electrolyte member disposed between the detecting electrode and the standard electrode, wherein the detecting electrode, the standard electrode and the electrolyte member constitute a sensor portion to measure hydrogen concentration within the hydrogen storage alloy as an electromotive force value.

In this aspect, the difference between chemical potentials of hydrogen stored in the detecting electrode, which is determined by its concentration, and hydrogen at the standard electrode is measured by the sensor portion as an electromotive force value between the detecting electrode and the standard electrode.

In a second aspect of the invention, the hydrogen storage vessel is operated to store hydrogen in the hydrogen storage alloy.

In this aspect, the hydrogen content within the hydrogen storage vessel is directly measured by the sensor portion.

In a third aspect of the invention, the hydrogen quantity sensor comprises at least two detecting electrodes respectively comprised of different hydrogen storage alloys made of different materials, so that at least two sensor portions are provided. In this aspect, the at least two sensor portions output different measurement values having different detecting characteristics, so that, by judging the measured values in a comprehensive manner, the hydrogen concentration can be defined.

In a fourth aspect of the invention, the at least two sensor portions are assembled within a single sensor holder.

In a fifth aspect of the invention, the electrolyte member is comprised of a solid electrolyte in which hydrogen ions or ions reactive with hydrogen are movable at a hydrogen delivery temperature range of the hydrogen storage alloy.

In a sixth aspect of the invention, the standard electrode is comprised of a material more active than that of the detecting electrode.

comprising seventh aspect of the invention is a hydrogen storage vessel, electrodes, and electrolyte member, which are arranged to directly detecting hydrogen amount contained within the hydrogen storage alloy.

An eighth aspect of the invention is a hydrogen amount display device comprising the hydrogen quantity sensor as defined in anyone of the present invention.

A ninth aspect of the invention is a hydrogen storage device comprising the hydrogen quantity sensor as defined in the present invention.

Effects of the Invention

According to the present invention, a quantitative measurement of hydrogen content in the hydrogen storage device, which utilizes the hydrogen storage alloy, has been realized

Figure 1:
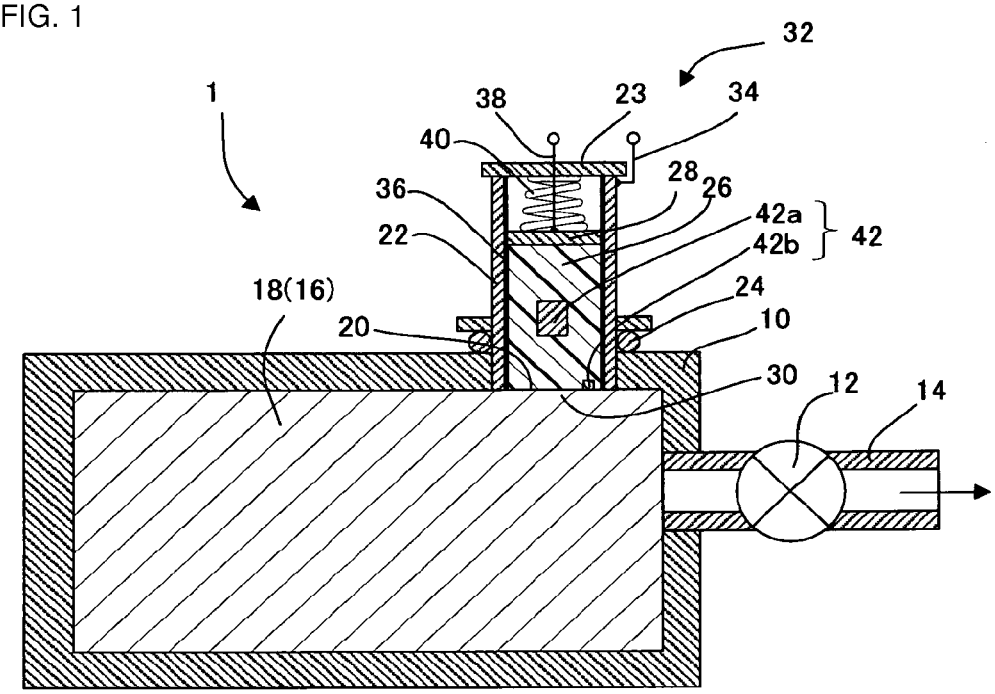
FIG. 1 is a schematic view of the hydrogen storage device having a hydrogen quantity sensor according to a first embodiment of the present invention.

BRIEF EXPLANATION OF THE NUMERALS 1 hydrogen storage device
10 hydrogen storage vessel
12 on-off valve
14 port
16 space
18 hydrogen storage alloy,
22 sensor holder
24 metal seal
26, 26a electrolyte member
28 standard electrode
30 detecting electrode
32a, 32b sensor portion
34 wire
36 insulating pipe
38 lead wire
40 compression spring
42 temperature adjusting device
42a micro-heater
42b temperature sensor
44 detecting alloy
50 controller
54 fuel meter
62 converter circuit

BEST MODE FOR CARRYING OUT THE INVENTION

The embodiments of the present invention will be described hereinafter with reference to the attached drawings. FIG. 1 is a view illustrating a first embodiment of the hydrogen storage device comprising a hydrogen quantity sensor according to the present invention. The hydrogen storage device 1 comprises: a cylindrical vessel 10 having one covered or sealed end; a port 14 provided on the other end of the vessel 10 and having an on-off valve 12; a hydrogen storage alloy (hydrogen storage portion) 18 contained within a space 16 inside the vessel 10; and a temperature adjustment device not shown in FIG. 1. The hydrogen storage alloy is exemplified by a $Mg_2Ni$ alloy (hydrogen delivery temperature: 250° C.), or TiFeNiZi based alloy (hydrogen delivery temperature 120-160° C.), etc.

An opening 20 is formed on a side portion of the wall of the vessel 10 to which a sensor holder 22 is coupled by threading. The sensor holder 22 is air-tightly formed and cylindrically shaped. The sensor holder 22 is attached to the vessel 10 via a sealing metal member 24. Inside the sensor holder 22, there are provided an electrolyte member 26 contacting the hydrogen storage alloy 18 within the vessel 10 and a standard electrode 28 contacting the outer edge of the electrolyte member 26. Thus, a sensor portion 32 is constructed by a detecting electrode 30, which is comprised of the hydrogen storage alloy 18 itself, the standard electrode 28 provided at outer side of the vessel 10, and the electrolyte member 26 sandwiched by these electrodes. The standard electrode 28 is preferably made of a stable electrode material that does not suffer from oxidations or corrosions at hydrogen delivery temperature (several hundreds ° C.) of the hydrogen storage alloy 18. It is also preferable to use materials inactive to hydrogen gas such as Ti of Ti alloys.

The sensor holder 22 is electrically conductive so as to function as an electric terminal from the detecting electrode 30 (hydrogen storage alloy 18) and is connected to an unshown voltmeter with a wire 34. On the inner surface of the sensor holder 22, an insulating pipe (insulating member) 36 is provided to electrically insulate the standard electrode 28 and detecting electrode 30 from the sensor holder 22. A lead wire 38 from the standard electrode 28 is drawn out to the outer space through a top plate 23 of the sensor holder 22. In a space between the standard electrode 28 and the top plate 23, a compression spring 40 is provided to push the standard electrode 28 and the electrolyte member 26 towards the vessel 10 for maintaining an electrical contact between the electrolyte member 26 and standard electrode 28 or the detecting electrode 30.

Since the hydrogen delivery temperature of the hydrogen storage alloy 18 is approximately between 100~300° C., the electrolyte member 26 is utilized, which is effective in such a temperature range by maintaining the ion conduction performance. The electrolyte member 26 may be made from any convenient materials in either solid or liquid state, and among others, solid electrolytes such as phosphorous tungstic acid are advantageous due to its easy-to-handle property and stable performances at a temperature range below 150° C. Phosphorous tungstic acid is also advantageous in having higher adhesion to the detecting electrode 30 or the standard electrode 28. The electrolyte member 26 may contain reinforcing materials such as glass wool in addition to the electrolyte material such as phosphorous tungstic acid. In this case, not only the strength of the electrolyte member 26 can be enhanced, but also the adhesion of the electrolyte member 26 to the electrodes can be further enhanced. In addition, for the temperature range above 200° C., an oxygen ion conductive solid electrolyte having reactivity with hydrogen is preferably replaceable.

The phosphorous tungstic acid and the phosphorous molybdic acid are normally obtained in the form of powder, so that in the fabrication of the solid electrolyte, the powdery phosphorous tungstic acid or phosphorous molybdic acid is solidified by compression molding into a pellet shape. However, the solid material thus compression molded is too fragile to be used for a long period of time as it is. Therefore, it is preferable to add some glass wool into a resolved phosphorous tungstic acid material, which is a solution of the powdery phosphorous tungstic acid in a given solvent (such as ion exchanged water), and to solidify it into a solid electrolyte. The manufacturing process of the solid electrolyte is described hereinafter. This process is also effective in enhancing the adhesion between the electrodes and the solid electrolyte.

(1) A powdery raw material for the intended solid electrolyte (such as phosphorous tungstic acid) is melted in a given solvent to be liquidized, (2) Reinforcing materials are put in a space within a mold for forming the solid electrolyte, and electrodes are assembled therein, (3) The liquidized raw material is flowed into the mold containing the reinforcing materials, (4) The liquidized raw material is solidified to form the solid electrolyte into a primitive form of the hydrogen gas sensor.

In this embodiment, a temperature adjustment device 42 comprising a micro heater 42a and a temperature sensor 42b is assembled in the electrolyte member 26, which are connected to an unshown controller, so as to control the temperature of the electrolyte member 26 at a hydrogen delivery temperature of the hydrogen storage alloy 18. This makes it possible to measure hydrogen content of the hydrogen storage device even in a room temperature range.

The hydrogen quantity sensor detects the residual amount of the hydrogen within the hydrogen storage alloy 18 based on the following principle. By arranging the electrolyte member 26 sandwiched between the hydrogen storage alloy 18 (detecting electrode 30) and the standard electrode 28, an electrochemical cell in a form of:

[I] Metal–H|H+electrolyte|Metal [II]

is formed, in which electromotive force (EMF) generated between the two electrodes [I] and [II] has the following relationship with the chemical potentials at the two the electrodes:

$$\mu_H^M - \mu_H^{H-H} = (\tilde{\mu}_e^{II} - \tilde{\mu}_e^I) - F(\phi_e^{II} - \phi_e^I) = -FE \quad (1)$$

wherein the character "F" represents the Faraday constant, the character "E" represents an EMF value, and $\mu_H^{M}-\mu_H^{M-H}$: respectively represent chemical potentials of the atomic hydrogen at the standard electrode 28 and the hydrogen storage alloy 18. Since the terminals [I] and [II] are made of the same copper wire, the electrochemical potentials of electron are represented by the following equation:

$$\tilde{\mu}_e^{II} = \tilde{\mu}_e^I \quad (2)$$

Herein, the following equation showing the relation between the electrostatic potential and the electromotive force E is employed:

$$\phi_e^{II} - \phi_e^I = E \quad (3)$$

The chemical potential of hydrogen has a following relationship with the free energy of the hydrogen within the hydrogen storage alloy 18:

$$\mu_H^M - \mu_H^{M-H} = \frac{\partial \Delta G}{\partial n} \quad (4)$$

wherein the character "G" represents Gibbs free energy, and the character "n" represents hydrogen concentration within the hydrogen storage alloy 18. If the hydrogen within the hydrogen storage alloy 18 is in a two-phase state (e.g., solid solution phase and hydride state), each phase has a different Gibbs free energy, however, the chemical potential of the hydrogen will be identical. This is because the potential differences of the hydrogen will cause movement of particle towards the low chemical potential phase. Thus, the two-phase state regions of the hydrogen storage alloy 18 also provide the identical electromotive force.

The electromotive force value obtained by the hydrogen quantity sensor of the present invention depicts the chemical potential difference of the atomic hydrogen at both electrodes. Since the chemical potential of hydrogen within the hydrogen storage alloy 18 is equal to that of the atomic hydrogen on the boundary surface of the hydrogen storage alloy 18 when they are in a thermal equilibrium state, the sensor can measure the chemical potential within the hydrogen storage alloy 18 by the above-described process.

As described above, since the electromotive force are output from the present sensor as an extensive physical value, the electromotive force does not depend on the physical size or the structure of the electrodes, and only depends on the electrodes' materials, so that the sensor of the present invention can be downsized and simplified.

The electrolyte member 26 is assigned with a function to transmit the information regarding the intensity of the chemical potential of hydrogen at the detecting electrode 30 and standard electrode 28. Therefore, the electrolyte member 26 can be well usable if it has sufficient hydrogen ion conduction or ion conduction for ions that have good reactivity with hydrogen.

In the hydrogen storage device shown in FIG. 1, the hydrogen quantity sensor outputs electromotive force corresponding the content of hydrogen stored in the hydrogen storage alloy 18, which is in contact with the electrolyte member 26, in accordance with the above-described principle, and the measured electromotive force is then converted into a hydrogen concentration value based on the preliminary obtained relationship for the electromotive force and hydrogen concentration. The electromotive force thus obtained is dependent on temperature because hydrogen free energy depends on temperature as described in the following equation:

$$G = H - TS \quad (5)$$

Therefore, it is necessary to measure the temperature of the hydrogen storage alloy 18 with a thermometer 41 to amend the measured EMF value. It is especially necessary to prepare a temperature/EMF relationship data in advance, because the hydrogen storage alloy 18 IS subjected to a large temperature variation ranging from a room temperature to the hydrogen delivery temperature. The micro heater 42a is provided for adjusting the temperature of the electrolyte member 26 at an operational range.

Figure 2:
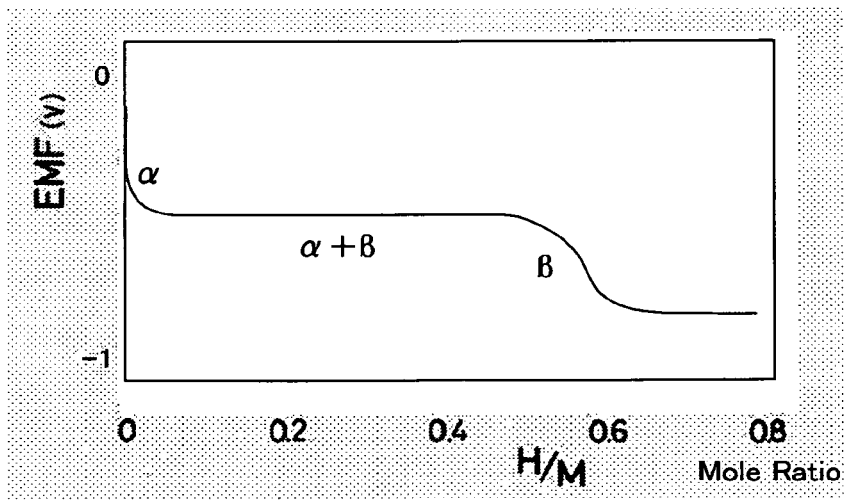
FIG. 2 is a graph showing an example of relationship between hydrogen concentration and electromotive force in the hydrogen quantity sensor illustrated in FIG. 1.

FIG. 2 illustrates an example of the relationship between the hydrogen concentration and the electromotive force value, in which the horizontal scale is assigned to hydrogen concentration (H/M: mole ratio) in the hydrogen storage alloy 18. In the schematic diagram for the hydrogen storage alloy 18 shown in FIG. 1, the hydrogen storage alloy 18 forms one hydride phase (β-phase) and an α-phase consisting of a hydrogen solid solution phase at a lower concentration range. In the 13-phase range, the EMF value varies dependent to the hydrogen concentration. The EMF constant range in the diagram shows that hydrogen within the alloy stays in two mixed phases (α-phase+β-phase). This means that the sensor portion 32 is effective only in a limited range of the β-phase where sufficient amount of hydrogen exists within the hydrogen storage alloy 18. In the mixed phase range (α-phase+β-phase) where remaining hydrogen has become scarce, it is no longer possible to detect hydrogen quantitatively. When entering into a single a-phase range, the EMF value also regains dependency on the hydrogen concentration. However, the hydrogen concentration is very small in the a-phase range and the remaining hydrogen fuel amount is already close to zero. Therefore, it will be necessary to urge refilling of hydrogen at the time when the sensor has detected the mixed phase range (α-phase+β-phase). The amount of the stored hydrogen is proportional with the volume or mass of hydrogen storage alloy 18.

In the embodiment, the range where H/M-O.5-O.O5 is a dead zone for the sensor, and the sensor is able to measure only in a high concentration range where H/M=0.5-0.7. Therefore, it is preferable to concomitantly use other measuring devices that can measure in the low concentration range, so that the whole concentration range can be covered. Other measuring devices include a flow integrator or the like.

Figure 3:
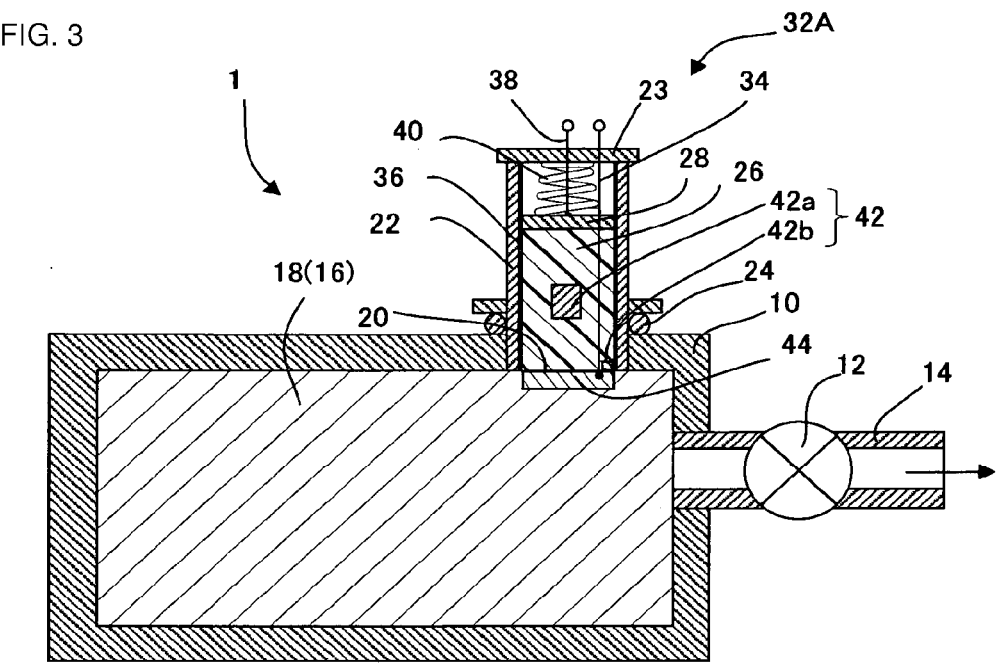
FIG. 3 is a schematic view of the hydrogen storage device having a hydrogen quantity sensor according to a second embodiment of the present invention.

FIG. 3 illustrates a hydrogen storage device 1 having the hydrogen quantity sensor according to a second embodiment of the present invention, in which the aforementioned problem of being ineffective in the two-phase range with α-phase-β-phase has been solved.

Figure 4:
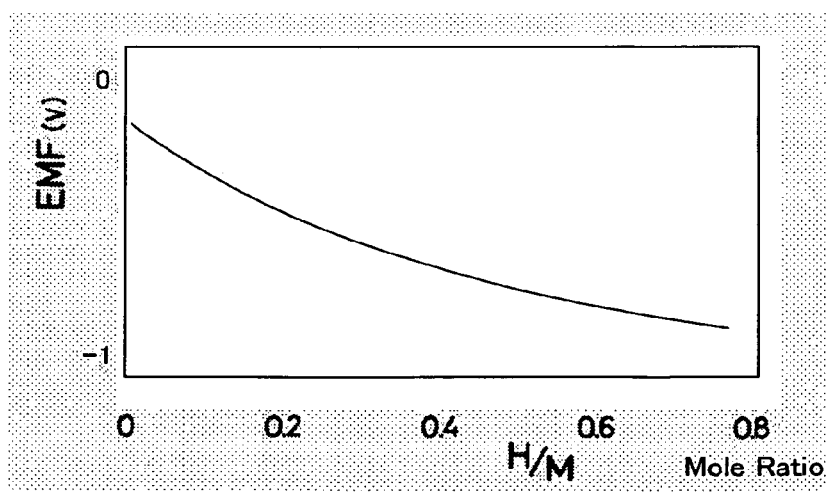
FIG. 4 is a graph showing an example of relationship between hydrogen concentration and electromotive force in the hydrogen quantity sensor illustrated in FIG. 3.

In this embodiment, a detecting alloy 44 comprised of a hydrogen storage alloy different from the hydrogen storage alloy 18 (storing alloy) is provided so that another sensor portion 32A using the detecting alloy as a detecting electrode 30 is formed. The material for the detecting alloy 44 is exemplified by Pd—H based alloys or PdAg—H alloys. This is because the Pd—H based alloy is single-phased in the whole hydrogen concentration range of H/M=0~1 at temperatures above 270° C., and the EMF value varies proportionally in the whole concentration range as shown in FIG. 4, so that it can cover the whole concentration range on its own. The detecting electrode 30 can be made by integrating Pd with the storing alloy 18 by plating or vapor depositing Pd on a portion of the hydrogen storage alloy 18, so that their contact is maintained. With this configuration, the sensor can indirectly measure the hydrogen concentration within the detecting object because the detecting electrode 30 and the hydrogen storage alloy 18 are in a thermal equilibrium state. The detecting electrode 30 of this embodiment can be very small in mass and shaped in a thin film having a sufficient surface area for covering the electrolyte member 26. The detecting electrode 30 can be also made by implanting a fragmentary specimen, which is made of the same material as the storing alloy 18 and is coated with a Pd film in the same manner as described above, into the hydrogen storage alloy 18. The hydrogen concentration of the hydrogen storage alloy 18 can be measured by measuring the hydrogen concentration within this specimen in a sampling manner.

As described above, since requirements are different for the storing alloy 18 and the detecting alloy 44, the use of different materials having respective suitable performances will provide a hydrogen storage device 1 with an effective hydrogen quantity sensor utilizing advantages of the respective materials.

Figure 5:
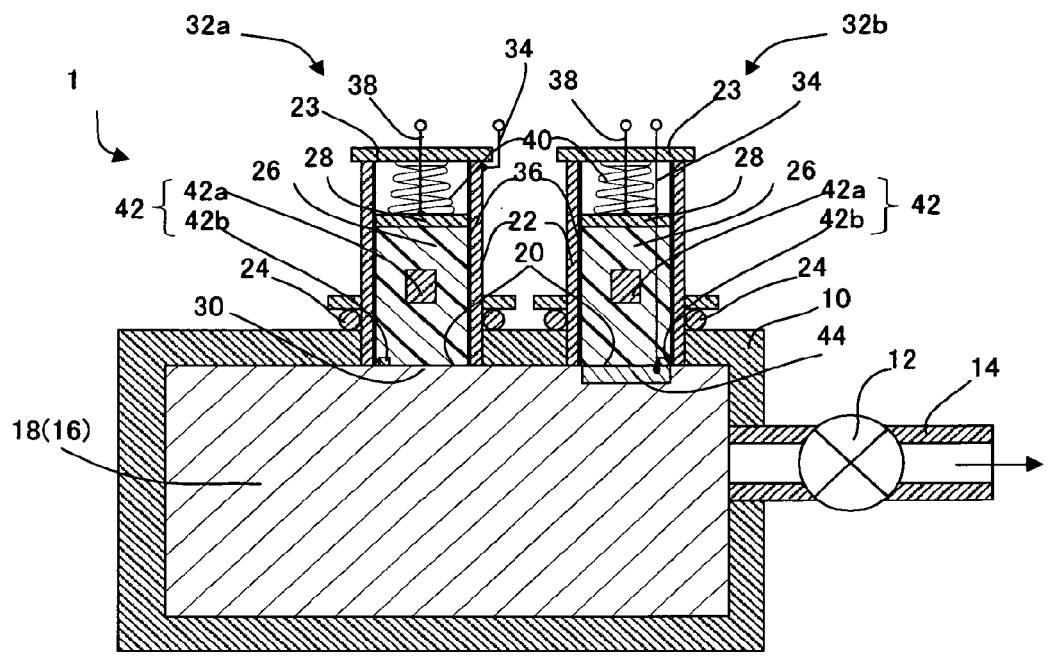
FIG. 5 is a schematic view of the hydrogen storage device having a hydrogen quantity sensor according to a third embodiment of the present invention.
Figure 6:
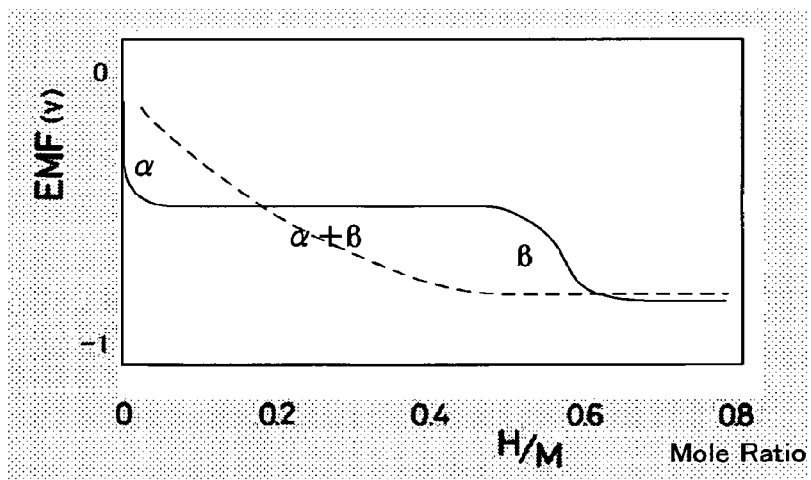
FIG. 6 is a graph showing an example of relationship between hydrogen concentration and electromotive force in the hydrogen quantity sensor illustrated in FIG. 5.

FIG. 5 illustrates a hydrogen storage device 1 having a hydrogen quantity sensor according to a third embodiment of the present invention. This is a composite type sensor simultaneously provided with the sensor portion 32 of the first embodiment and the sensor portion 32b of the second embodiment. That is, a first sensor portion 32a using the storing alloy 18 as a detecting electrode 30, and a second sensor portion 32b using the detecting alloy 44 made of a different material as a detecting electrode 30, are provided in parallel. This configuration is effective when combining the sensor portions 32a, 32b having respective dead zones at different concentration ranges from each other. In this embodiment, the first sensor portion 32a covers a high concentration range, and the second sensor portion 32b covers a low concentration range so that the sensor covers the whole range.

While the first sensor portion 32a uses the storing alloy 18 as a detecting electrode 30 and the second sensor portion 32b uses a detecting alloy 44 in this embodiment, it is possible to combine two sensor portions using two detecting alloys made of different materials other than the storing alloy 18. Further, the number of the sensor portions 32a, 32b is not limited to two, and it is possible to assemble three or more sensor portions.

Figure 7:
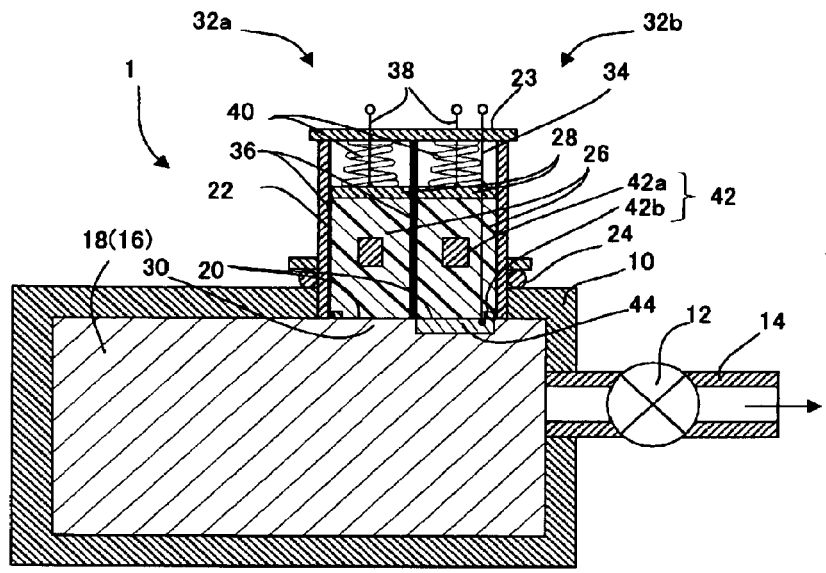
FIG. 7 is a schematic view of the hydrogen storage device having a hydrogen quantity sensor assembled with a complementary hydrogen detecting sensor according to a fourth embodiment of the present invention.

FIG. 7 illustrates a hydrogen storage device 1 having the hydrogen quantity sensor according to a fourth embodiment of the present invention, in which the two sensor portions 32a, 32b are assembled in one sensor holder 22 so as to make a module. This modification can facilitate easy assembling of the sensor portions, enhancement of performance of the sensor as well as reduction of the manufacturing cost. Since this embodiment functions in the same manner as that of FIG. 5, the detailed explanation will be omitted.

Figure 8:
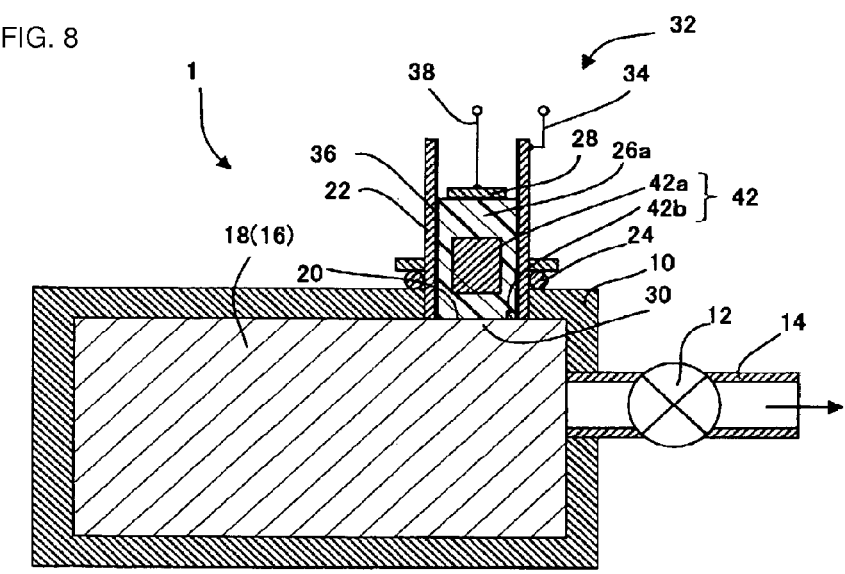
FIG. 8 is a schematic view of the hydrogen storage device having a hydrogen quantity sensor according to a fifth embodiment of the present invention.

FIG. 8 illustrates a hydrogen storage device 1 having a hydrogen quantity sensor according to a fifth embodiment of the present invention. Here, the electrolyte member 26a is made of a hydrogen impermeable material and the standard electrode 28 is selected from the metal having a higher chemical potential relative to hydrogen such as Pt or Pt alloys, so that the sensor can function as a hydrogen leakage detecting sensor. The hydrogen impermeable material for the electrolyte member 26 is exemplified by a ceramic type oxygen ion conductor. In this embodiment, if hydrogen leakage occurs and hydrogen chemical potential at the standard electrode 28 reaches as high as or close to that of the interior of the hydrogen storage alloy 18, an intensive counter electromotive force is generated. Thus, the hydrogen gas leakage can be detected by detecting such counter electromotive force.

Figure 9:
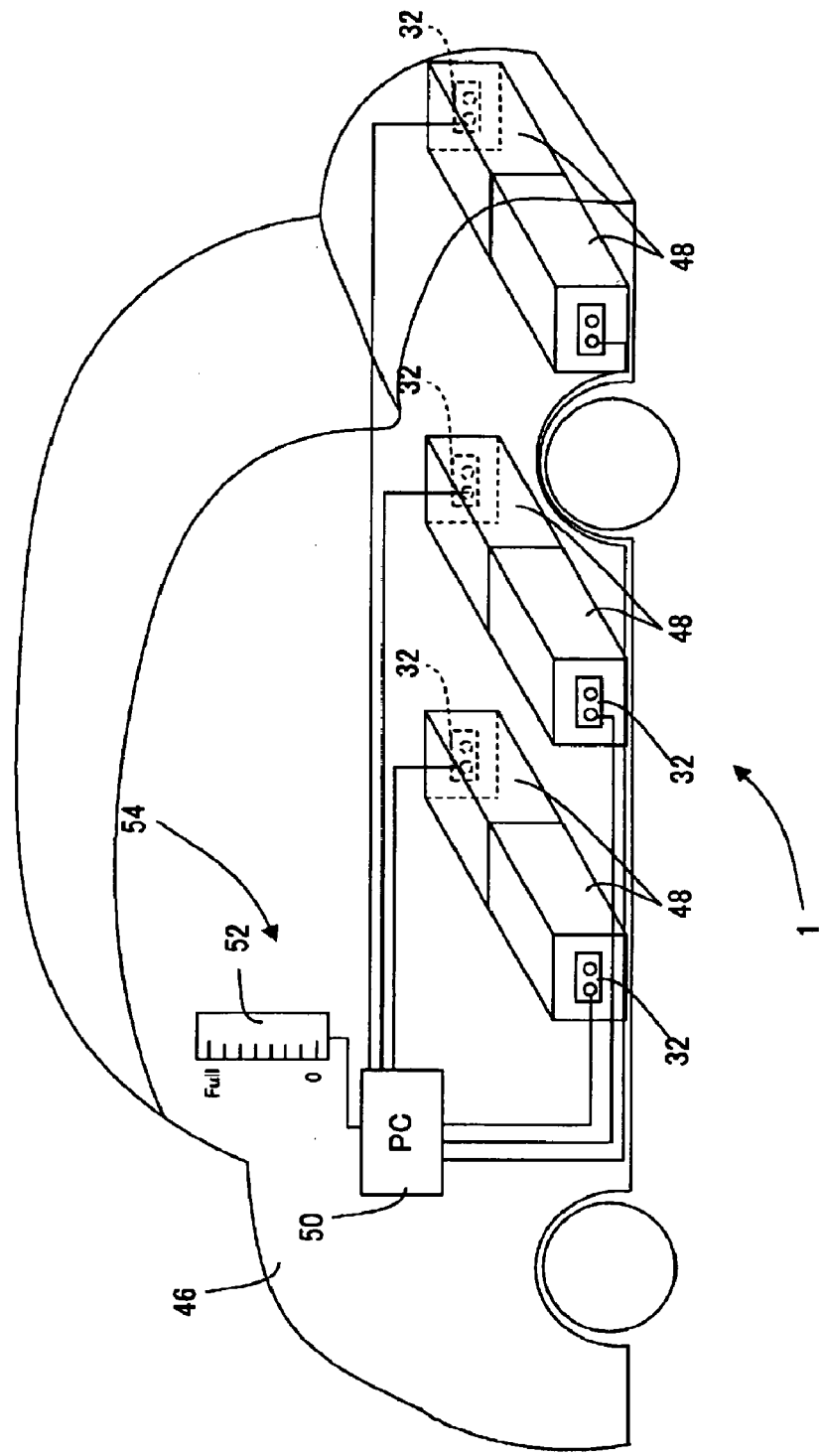
FIG. 9 is a schematic explanatory view of a fuel storage device for automobile using the hydrogen quantity sensor according the present invention.

FIG. 9 illustrates a hydrogen storage device 1 having a hydrogen quantity sensor of the present invention and being applied for a fuel tank for an automobile. The hydrogen storage device 1 comprises plural (6 in the drawing) cartridges 48 loaded on the automobile 46 for storing hydrogen, each of which comprises a sensor portion 32 (32A, 32a, 32b) according to the present invention. The output signals from the sensor portions 32 are input into the computer 50 serving as a controller so that the computer 50 displays the output signal on a display 52 provided on a front panel of the automobile 46. The sensor portions 32, the computer 50 and the display 52 constitute a fuel meter (hydrogen amount display device) 54.

Figure 10:
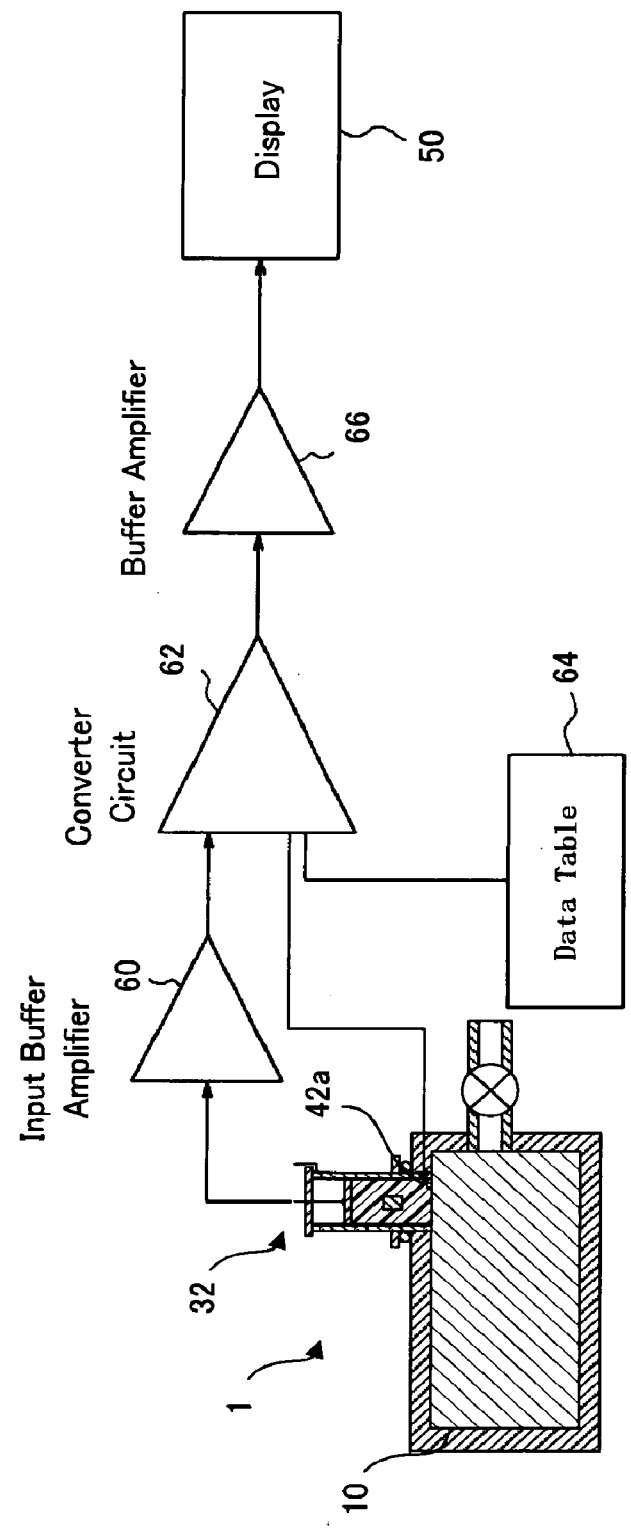
FIG. 10 is a block diagram of the fuel meter using the hydrogen quantity sensor according an embodiment of the present invention.

FIG. 10 is a block diagram illustrating the function of the fuel meter 54. The electromotive force variation as a hydrogen gas detecting information from the sensor portion 32 is input into an input buffer amplifier 60 of a high input impedance, converted in impedance and signal level, and further input into a converter circuit 62 at a next stage. In the converter circuit 62, a data table 64 is preliminarily stored in which the electromotive force output from the sensor portion 32 and the residual hydrogen amount within the hydrogen storage device 1 are coordinated at each temperature. Therefore, the converter circuit 62 calculates residual hydrogen amount from the electromotive force output from the hydrogen quantity sensor 10 and the temperature signal output from the temperature sensor 42a by referring to the data table 64, and sends the output value to the display 68 on the front panel of the automobile via the buffer amplifier 66 for displaying it. It is preferable to issue a warning signal in a predetermined form when the residual amount is lowered below a certain level.

Although the present invention has been described in detail with reference to the above examples, this invention is not limited to the above disclosure and every kind of variation and modification may be made without departing from the scope of the present invention.

The invention claimed is:

1. A hydrogen quantity sensor comprising:
   a first sensor portion which detects hydrogen concentration in a high concentration range; and
   a second sensor portion which detects hydrogen concentration in a low concentration range,
   wherein each of the first sensor portion and the second sensor portion comprises:
   (i) a detecting electrode comprised of a hydrogen storage alloy disposed inside a hydrogen storage vessel;
   (ii) a standard electrode disposed confronting the detecting electrode; and
   (iii) an electrolyte member disposed between the detecting electrode and the standard electrode,
   wherein each of the sensor portions measures an electromotive force value, and
   wherein the detecting electrode of the first sensor portion is comprised of a different hydrogen storage alloy than the detecting electrode of the second sensor portion.

2. The hydrogen quantity sensor of claim 1, wherein said first sensor portion and said second sensor portion are assembled within a single sensor holder.

3. The hydrogen quantity sensor of claim 1, wherein the standard electrode is comprised of a material more active than that of the detecting electrode.

4. The hydrogen quantity sensor of claim 1, wherein the hydrogen storage vessel, electrodes, and electrolyte members are arranged to directly detect hydrogen amount contained within the hydrogen storage alloys.

5. A hydrogen amount display device comprising the hydrogen quantity sensor as defined in claim 1.

6. A hydrogen storage device comprising the hydrogen quantity sensor as defined in claim 1.

* * * * *